(12) United States Patent
Kim et al.

(10) Patent No.: US 9,198,583 B2
(45) Date of Patent: Dec. 1, 2015

(54) METHOD AND APPARATUS FOR CORRECTING ERROR IN BLOOD PRESSURE MEASUREMENT

(75) Inventors: Youn-ho Kim, Yongin-si (KR); Seok-chan Kim, Yongin-si (KR); Kun-soo Shin, Yongin-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 979 days.

(21) Appl. No.: 12/723,903

(22) Filed: Mar. 15, 2010

(65) Prior Publication Data
US 2010/0274142 A1 Oct. 28, 2010

(30) Foreign Application Priority Data
Apr. 28, 2009 (KR) .................. 10-2009-0037109

(51) Int. Cl.
*A61B 5/02* (2006.01)
*A61B 5/022* (2006.01)
*A61B 5/021* (2006.01)

(52) U.S. Cl.
CPC .............. *A61B 5/022* (2013.01); *A61B 5/02108* (2013.01); *A61B 5/02225* (2013.01)

(58) Field of Classification Search
USPC ................................... 600/490, 494
See application file for complete search history.

(56) References Cited

U.S. PATENT DOCUMENTS

| | | | | |
|---|---|---|---|---|
| 4,464,123 | A | * | 8/1984 | Glover et al. ................ 434/268 |
| 5,577,508 | A | * | 11/1996 | Medero .......................... 600/494 |
| 6,733,462 | B1 | * | 5/2004 | Frick et al. .................... 600/503 |
| 2007/0066910 | A1 | * | 3/2007 | Inukai et al. ................. 600/513 |

FOREIGN PATENT DOCUMENTS

| | | |
|---|---|---|
| JP | 05-192300 | 8/1993 |
| JP | 06-296591 | 10/1994 |
| JP | 06-319708 | 11/1994 |
| JP | 07-039530 | 2/1995 |
| JP | 07-124130 | 5/1995 |
| JP | 1998071129 A | 3/1998 |
| JP | 2001070262 A | 3/2001 |
| JP | 2006-247220 | 9/2006 |
| KR | 10-2002-0059735 | 7/2002 |

OTHER PUBLICATIONS

Korean Office Action with English Translation for Application No. 10-2009-0037109 dated May 7, 2015.

* cited by examiner

*Primary Examiner* — Navin Natnithithadha
*Assistant Examiner* — Michael R Bloch
(74) *Attorney, Agent, or Firm* — Cantor Colburn LLP

(57) ABSTRACT

A method of correcting an error in a measured blood pressure includes measuring a blood pressure at a first site of a first body, calculating, using a processor, the error in the blood pressure measured at the first site of the first body based on a correlation between a shape of a sphygmogram measured at a first body part and a difference between a blood pressure measured at the first body part and a blood pressure measured at a second body part, where the correlation is predetermined using a statistical method based on a plurality of data from the blood pressure measured at the first body part and the blood pressure measured at the second body part, and correcting, using the processor, the blood pressure measured at the first site of the first body using the error calculated based on the correlation.

11 Claims, 8 Drawing Sheets

◆ DIASTOLIC BLOOD PRESSURE INDEX-ERROR CORRELATIONS (72)
■ SYSTOLIC BLOOD PRESSURE INDEX-ERROR CORRELATIONS (71)

METHOD AND APPARATUS FOR CORRECTING ERROR IN BLOOD PRESSURE MEASUREMENT

CROSS-REFERENCE TO RELATED APPLICATION

This application claims priority to Korean Patent Application No. 10-2009-0037109, filed on Apr. 28, 2009, and all the benefits accruing therefrom under 35 U.S.C. §119, the content of which in its entirety is herein incorporated by reference.

BACKGROUND

1) Field

The general inventive concept relates to a method and apparatus which measures blood pressure and corrects an error in blood pressure measurement.

2) Description of the Related Art

Blood pressure is a type of index of a person's health condition. Apparatuses for measuring blood pressure are commonly used in medical institutions and at home. The U.S. Food and Drug Administration ("FDA") requires that the standards for the approval of blood pressure measurement apparatuses comply with the requirements of the Association for the Advancement of Medical Instrumentation ("AAMI"). American National Standards Institute ("ANSI")/AAMI SP10 Manual, for electronic or automated sphygmomanometers, issued by the AAMI, offers specification details and safety and performance requirements for blood pressure measurement apparatuses. When pressure is applied to a body site where arterial blood flows to stop the flow of blood, and the pressure is then is gradually released, a pressure when an initial pulse is heard, referred to as systolic blood pressure, and a pressure when no more pulse is heard, referred to as diastolic blood pressure are obtained. Alternatively, a digital blood pressure device may calculate blood pressure by detecting a waveform measured when pressure is applied to a body part.

SUMMARY

An aspect of the present invention includes a method and apparatus that corrects an error in blood pressure measurement and thereby substantially increases accuracy of the blood pressure measurement.

An aspect of the present invention includes a computer program product including a computer readable computer program code for executing the method of correcting an error in a measured blood pressure and instructions for causing a computer to implement the method.

Additional aspects will be set forth in part in the description which follows and, in part, will be apparent from the description, or may be learned by practice of the following description.

According to an aspect of the present invention, a method of correcting an error in a measured blood pressure, includes calculating the error in the measured blood pressure, which is measured at a first site of a first body based on a correlation between a shape of sphygmogram measured at a first body part and a difference between blood pressure measured at the first body part and blood pressure measured at a second body part, and correcting the blood pressure measured at the first site of the first body using the error calculated based on the correlation, where the first body part is one of the first site of the first body and a first site of a second body which is a same body part as the first site of the first body, and the second body part is one of a second site of the first body and a second site of the second body.

According to an aspect of the present invention, a computer program product comprising a computer readable computer program code for executing a method of correcting an error in a measured blood pressure, and instructions for causing a computer to implement the method, the method comprising: calculating the error in the measured blood pressure, which is measured at a first site of a first body, based on a correlation between a shape of sphygmogram measured at a first body part and a difference between blood pressure measured at the first body part and blood pressure measured at a second body part; and correcting the blood pressure measured at the first site using the error calculated based on the correlation, wherein the first body part is one of the first site of the first body and a first site of a second body, which is a same body part as the first site of the first body, and the second body part is one of a second site of the first body and a second site of the second body.

According to an aspect of the present invention, an apparatus for measuring blood pressure includes a sensing unit which senses a sphygmogram at a first site of a first body, a correction unit which corrects an error of blood pressure, which is calculated using the sphygmogram sensed at the first site of the first body, based on a correlation between a shape of the sphygmogram measured at a first body part and a difference between blood pressure measured at the first body part and blood pressure measured at a second body part, and an output unit which displays a corrected blood pressure, where the first body part is one of the first site of the first body and a first site of a second body which is a same body part as the first site of the first body, and the second body part is one of a second site of the first body and a second site of the second body.

BRIEF DESCRIPTION OF THE DRAWINGS

The above and/or other aspects of the general inventive concept will become more readily apparent by describing in further detail embodiments thereof with reference to the accompanying drawings, in which.

DETAILED DESCRIPTION

Figure 1:
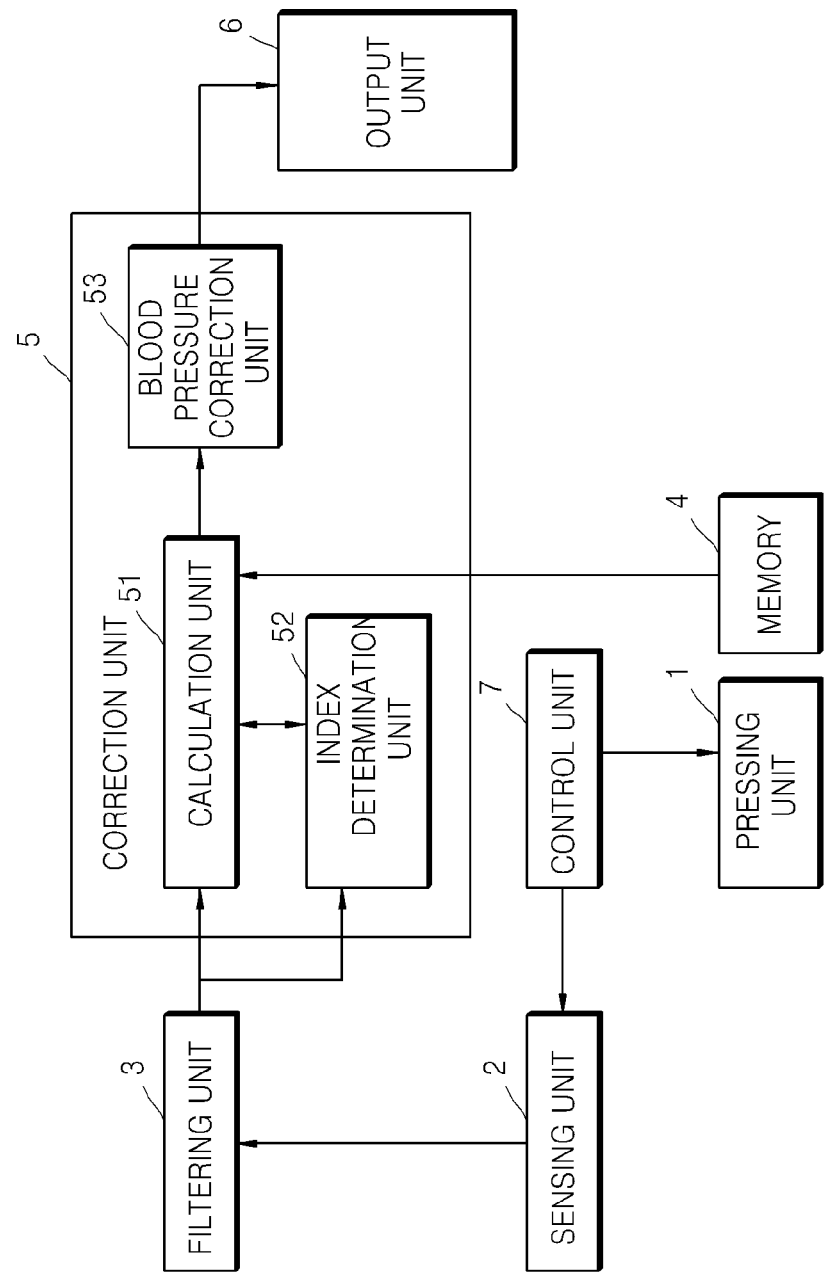
FIG. 1 is a block diagram illustrating structure of an embodiment of a blood pressure measuring apparatus.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments of the general inventive concept will be described in further detail with reference to the accompanying drawings.

FIG. 1 is a block diagram illustrating an embodiment of a blood pressure measuring apparatus.

As shown in FIG. 1, the blood pressure measuring apparatus includes a pressing unit 1, a sensing unit 2, a filtering unit 3, memory 4, a correction unit 5, an output unit 6 and a control unit 7. In an embodiment, the correction unit 5 which corrects an error in measured blood pressure may be included in the blood pressure measuring apparatus which may be a blood pressure instrument/blood pressure meter, a blood pressure measuring device or a hemadynamometer, for example. In another embodiment, the correction unit 5 may be separated from the blood pressure measuring apparatus as an independent error correction device. Hereinafter, hardware components related to an embodiment will be described in order to avoid unclear explanation thereof. However, it will be understood that other hardware components may also be included along with the hardware components in FIG. 1.

Based on a correlation between a shape of a sphygmogram measured at a first body part and a difference between blood pressure measured at the first body part and blood pressure measured at a second body part, the blood pressure measuring apparatus corrects an error in a measured blood pressure, which is measured at a first site of a first body, and thereby substantially increases the accuracy of the measured blood pressure. The first body part is a first site of a body, e.g., the first site of the first body or a first site of a second body, and the second body part is a second site of the body, e.g., a second body site of the first body or a second body site of the second body. As blood is pumped throughout a body by the heart, the blood pressure and the sphygmogram may be measured with respect to blood using the blood pressure measuring apparatus.

The blood pressure is pressure on the walls of blood vessels as blood pumped out of the heart flows along the blood vessels, and includes arterial blood pressure, capillary blood pressure, and venous blood pressure, for example, according to locations of blood vessels where blood pressure is measured. The blood pressure varies with heartbeats. Also, the blood pressure includes systolic blood pressure when blood flows into the arteries as the ventricles of the heart contract and diastolic blood pressure on the arterial walls due to the elasticity of the arterial walls even when the ventricles expand and blood stays in the ventricles.

The sphygmogram (or sphygmus wave) is a waveform when a pulse reaches peripheral nerves. The pulse is a phenomenon whereby the pressure of bloodstream flowing into the aorta due to heartbeats affects other arteries. That is, whenever the heart contracts, the heart delivers blood to every part of the body through the aorta and the pressure on the aorta varies. A variation of pressure reaches peripheral arterioles of the hands and feet. The sphygmogram shows the variation of pressure in a waveform. It will be understood that the blood pressure measuring apparatus may measure at least one of the sphygmogram and the pressure on the walls of the blood vessels in order to measure the blood pressure. Hereinafter, a blood pressure measuring method refers to a method of measuring at least one of blood pressure and a sphygmogram.

The blood pressure measuring apparatus may measure the blood pressure using an invasive or a noninvasive method. The invasive method includes directly inserting a catheter into a blood vessel, and connecting the catheter to a manometer to measure the blood pressure. The noninvasive method includes winding a cuff around one site, e.g., an upper arm, to measure blood pressure, pumping air into the cuff to press the one site, and measuring blood pressure when blood in one of a brachial artery and a radial artery stops flowing. The noninvasive method measures the blood pressure from outside the blood vessels.

Examples of the noninvasive method include, for example, an auscultatory method of measuring blood pressure using Korotkoff sounds, an oscillometric method of measuring blood pressure using oscillations generated from the flow of blood, a tonometeric method using a tonometer, and a method using pulse transit time ("PTT").

The invasive method includes the direct insertion of the catheter into the blood vessel, and the blood pressure is thereby substantially accurately and continuously measured. However, a blood pressure measuring method using the invasive method includes the inserting the catheter into the blood vessel to measure blood pressure. An embodiment of the blood pressure measuring apparatus may conveniently measure the blood pressure using the noninvasive method and may substantially increase the accuracy of the measured blood pressure using the correction unit 5 of the blood pressure measuring apparatus. Based on the correlation between the shape of sphygmogram measured at the first site of the body and the difference between the blood pressure measured at the first body part and the blood pressure measured at the second body part, the correction unit 5 corrects the error in the blood pressure measured at the first site of the first body and thereby substantially increases the accuracy of the measured blood pressure. In an embodiment, the blood pressure measured at the first body may be corrected using the blood pressure measured at another body. The blood pressure measured at the second body part may be defined as a reference blood pressure and the blood pressure measured at the first body part is compared to the reference blood pressure. Based on the result from comparison thereof, the difference between the blood pressure measured at the first body part and the blood pressure measured at the second body part is defined as an error. The blood pressure measured at the first site of the first body may be corrected using the correlation between the error and the shape of sphygmogram measured at the first body part. In an embodiment, the reference blood pressure may be measured at the second body part using one of the invasive method and the noninvasive method. It will be understood that, if the reference blood pressure is measured at the second body part using the invasive method to correct the blood pressure measured at the first site of the first body using the noninvasive method, the first and second sites of the body may be a same site. In an embodiment, the first site of the body may be the same as the second site of the body. In an embodiment, both of the first site and the second site may be a wrist.

In an noninvasive method, e.g., the auscultatory method, a body site where arterial blood flows is substantially sufficiently pressed to stop the flow of arterial blood and then is released, pressure at a moment when an initial pulse is heard is measured as the systolic blood pressure and pressure at a moment when no more pulse is heard is measured as the diastolic blood pressure.

Other methods, e.g., the oscillometric method and the tonometric method, may be used in digital blood pressure measuring apparatuses. Similarly to the auscultatory method, the oscillometric method measures the systolic blood pressure and the diastolic blood pressure by sensing oscillations of blood vessels generated when the flow of arterial blood at a body site are blocked by pressing on the body site and flowed by releasing the body site. In the tomometric method, blood pressure may be continuously measured using the amplitude and shape of a sphygmogram generated when a pressure that does not completely stop the flow of arterial blood is applied on a body site.

A convenient and portable digital automatic hemadynamometer may measure blood pressure using the noninvasive method. In an embodiment, one body part, at which blood pressure is measured, is pressed and blood pressure is calculated using variations of the amplitude of a sphygmogram and variations of the shape of the sphygmogram. The digital automatic hemadynamometer includes, e.g., a wrist-type hemadynamometer, a finger-type hemadynamometer, etc., according to body sites to be pressed.

It will be understood that the blood pressure measuring apparatus may include all blood pressure measuring methods using the noninvasive method and may be one of a wrist-type hemadynamometer and a finger-type hemadynamometer, and thereby substantially increases the accuracy of blood pressure measured. In an embodiment, an accuracy of a hemadynamometer, e.g., a wrist-type hemadynamometer, a finger-type hemadynamometer, which conveniently and continuously measures blood pressure, is substantially increased without additional hardware.

The pressing unit 1 presses a site of the body, at which blood pressure is to be measured. The pressing unit 1 may include a presser, e.g., a cuff or a wrist band, which presses, e.g., applies pressure to, the body part and an actuator which drives the presser to expand or contract. The body part includes any body site which has a blood vessel and at which blood pressure is measurable using the above-described blood pressure measuring methods, such as an upper arm having the brachial artery, or a wrist having the radial artery, a finger or a forearm, for example. In an embodiment, the pressing unit 1 may be controlled by the control unit 7, and thereby allows the presser to expand or contract using the actuator which presses the body part, such as the forearm, the upper arm, the wrist, or the finger, e.g., to measure the blood pressure.

The sensing unit 2 senses pressures and a sphygmogram in a blood vessel at the pressed site using at least one sensor when the site is pressed. In an embodiment, a pressure sensor may be used as the at least one sensor, but additional embodiments are not limited thereto. In an embodiment, the sensor may be any apparatus which detects pressures in a blood vessel. In an embodiment, the sensing unit 2 senses the pressure and the sphygmogram in the blood vessel of the site pressed by the pressing unit 1.

In an embodiment, the pressing unit 1 gradually increases the pressure at the site and, when the pressure reaches a pre-set value, the pressing unit 1 stops pressing the site. The pre-set pressure is a value when the flow of arterial blood stops and may be set by a user according to an operation environment. The sensing unit 2 measures the pressure and the sphygmogram in the blood vessel of the site pressed for a period of time, for example, from before or when the pressing unit 1 presses the site until after the pressing unit 1 stops pressing the one site. In an embodiment, the period of time may be arbitrarily set by a user and may be set to be a period from when arterial blood stops flowing until when arterial blood normally circulates. The sensing unit 2 measures the pressures in the blood vessel for the period of time and transmits the measured pressures to the filtering unit 3.

The filtering unit 3 passes high-frequency band components of the pressures sensed by the sensing unit 2, removes noise components of the pressures, and transmits the high-frequency band components to the correction unit 5. The filtering unit 3 may pass a signal of a frequency band higher than a boundary frequency without reducing the signal, and may reduce a signal of a cutoff frequency band lower than the boundary frequency. The pressures sensed by the sensing unit 2 include high-frequency band and low-frequency band components. Since the blood pressure measuring apparatus uses the high-frequency band components of the pressures, the low-frequency band components are removed by a high pass filter. The filtering unit 3 may include a general high pass filter. However, it will be understood that, according to an operation environment, when the pressures of the high-frequency band components are calculated using the low-frequency band components, the filtering unit 3 may include both a high pass filter and a low pass filter.

The filtering unit 3 will be described hereinafter in further detail with reference to FIG. 2.

Figure 2A:
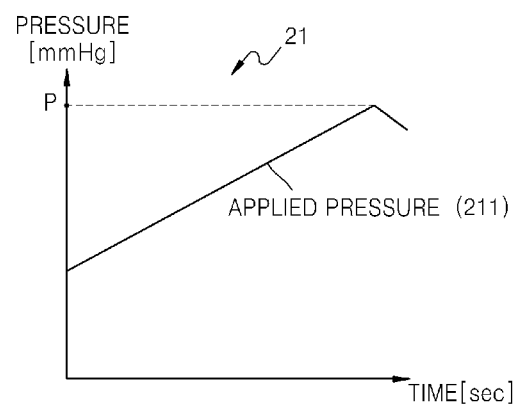
FIG. 2A is a graph illustrating pressure versus time of a pressure applied to a one site of a body by a pressing unit of the blood pressure measuring apparatus of FIG. 1.
Figure 2B:
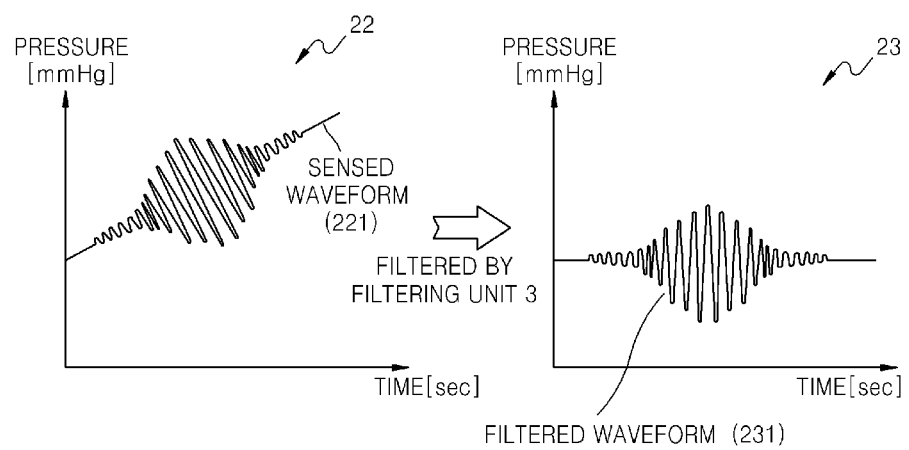
FIG. 2B is graphs illustrating pressure versus time of a sphygmogram including a sensed waveform of pressure sensed by the sensing unit of FIG. 1 when the pressure is applied to the one site, and pressure versus time of a sphygmogram including a filtered waveform of the sensed waved form filtered by the filtered unit 3 of FIG. 1.

FIG. 2A is a graph illustrating pressure versus time of a pressure applied to a one site of a body by the pressing unit 1 of FIG. 1, FIG. 2B is graphs illustrating pressure versus time of a sphygmogram including a sensed waveform of pressure sensed by the sensing unit of FIG. 1 when the pressure is applied to the one site, and pressure versus time of a sphygmogram including a filtered waveform of the sensed waveform filtered by the filtering unit 3 of FIG. 1

The graph 21 of FIG. 2A illustrates increasing and decreasing of the pressure applied on the one site at which blood pressure is measured by the pressing unit 1. As described above in relation to FIG. 1 and shown in the graph 21 of FIG. 2, applied pressure 211 applied by the pressing unit 1 of FIG. 1 is increased to a pre-set value P and decreased thereafter. A first graph 22 of FIG. 2B illustrates the sensed waveform 221 which includes the sphygmogram when a pressure applied to a one site of a body. The sensed waveform 221 sensed by the sensing unit 2 of FIG. 1 includes both high-frequency band components and low-frequency band components. A second graph 23 of FIG. 2B illustrates the filtered waveform 231 of the filtering unit 3 of FIG. 1 which filters the sensed waveform 221. In an embodiment, the filtering unit 3 includes a high pass filter, the filtering unit 3 passes a high-frequency signal of the sensed waveform 221 and reduces a low-frequency signal of the sensed waveform 221. Thus, values sensed by the sensing unit 2 are filtered by the filtering unit 3 and thereby form the filtered waveform 231 having the high-frequency band components.

Referring back to FIG. 1, the memory 4 is a general storing medium and previously stores an error correction equation calculated based on the correlation between a shape of the sphygmogram measured at the first body part and the difference between the blood pressure measured at the first body part and the blood pressure measured at the second body part. It will be understood that the memory 4 includes any one of a general storing medium, a recording medium and a unit which stores information in a general device. In an embodiment, the first body part may be the wrist having the radial artery, and the second body part be the upper arm having the brachial artery. The error correction equation may be previously stored in the memory 4 when the blood pressure measuring apparatus is manufactured, and the error correction equation may be changed by, for example, upgrading software after the blood pressure measuring apparatus is manufactured. A method of calculating an error correction equation will be described in detail later along with a description of the correction unit 5.

Based on the correlation between a shape of the sphygmogram measured at the first body part and the difference between the blood pressure measured at the first body part and the blood pressure measured at the second body part, the correction unit 5 corrects the error in the blood pressure measured at the first site of the first body. The correction unit 5 includes a calculation unit 51, an index determination unit 52 and a blood pressure correction unit 53. It will be understood that the correction unit 5 including the calculation unit 51, the index determination unit 52 and the blood pressure correction unit 53 may be separated from the blood pressure measuring apparatus as an independent error correction device. In an embodiment, the correction unit 5 may correspond to one processor or a plurality of processors of the blood pressure measuring apparatus. A processor may include at least one of an array of a plurality of logic gates and a combination of a general-use micro processor and memory which stores a computer programs to be executed in the micro processor. It will be understood that the processor may include a different type of hardware.

The calculation unit 51 calculates a blood pressure, an error, and a corrected blood pressure using the sphygmogram measured at the first site of the first body, which is obtained from the filtering unit 3.

Figure 3:
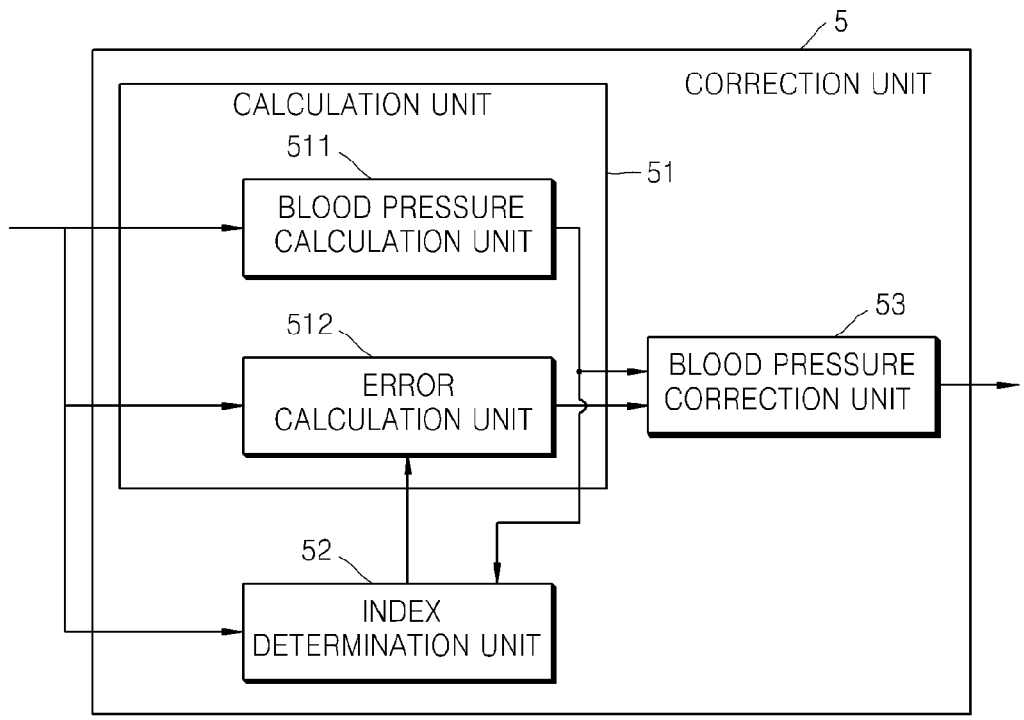
FIG. 3 is a block diagram illustrating an embodiment of a correction unit of the blood pressure measuring apparatus in FIG. 1.

FIG. 3 is a block diagram showing an embodiment of the correction unit 5 of the blood pressure measuring apparatus. The correction unit 5 of FIG. 3 will be described in conjunction with FIG. 1.

As shown in FIG. 3, the correction unit 5 includes the calculation unit 51, the index determination unit 52 and the blood pressure correction unit 53. The calculation unit 51 includes a blood pressure calculation unit 511 and an error calculation unit 512.

Figure 4:
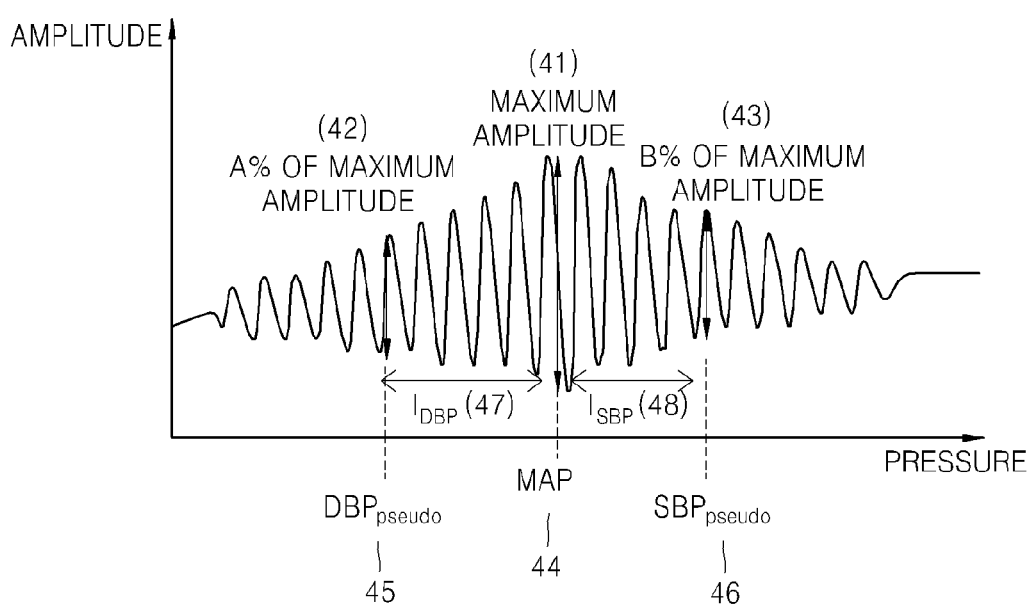
FIG. 4 is a graph illustrating an embodiment of a waveform measured at one site of a body.

FIG. 4 is a graph illustrating amplitude versus pressure of a waveform measured at the one site of a body according to the present invention. Although an embodiment using an oscillometric method as a blood pressure measuring method will now be described hereinafter, as described above, a blood pressure measuring method of an embodiment is not limited to the oscillometric method.

In FIG. 4, the graph shows a correlation between pressure and amplitude of the filtered waveform 231.

A pressure value where a sphygmogram has maximum amplitude 41 is referred to as mean arterial pressure ("MAP") 44. The mean arterial pressure 44 corresponds to a point where pressure applied by the pressing unit 1 of FIG. 1 is substantially equal to pressure of a blood vessel, which is sensed by the sensing unit 2 of FIG. 1. In a conventional blood pressure measuring apparatus, diastolic blood pressure and systolic blood pressure are calculated using a characteristic ratio with reference to the mean arterial pressure 44 of the sphygmogram. In an embodiment, to distinguish blood pressure before correction from blood pressure after correction, the diastolic blood pressure before correction and the systolic blood pressure before correction are respectively referred to as pseudo diastolic blood pressure ("$DBP_{pseudo}$") 45 and pseudo systolic blood pressure ("$SBP_{pseudo}$") 46. Points having pre-set ratios with respect to the maximum amplitude 41 may be defined as the diastolic blood pressure and the systolic blood pressure. That is, a pressure where the sphygmogram has A percent (%) the second 42 of the maximum amplitude 41 may be defined as the pseudo diastolic blood pressure 45 and a pressure where the sphygmogram has B % 43 of the maximum amplitude 41 may be defined as the pseudo systolic blood pressure 46. In an embodiment, the characteristic ratios such as A % 42 and B % 43 may be variously set according to an operation environment by a manufacturer or a user of the blood pressure measuring apparatus illustrated in FIG. 1. In an embodiment, the A % 42 and the B % 43 may be respectively set as 70% and 40%. That is, a pressure value where the sphygmogram has 70% of the maximum amplitude 41 may be defined as the pseudo diastolic blood pressure 45 and a pressure value having 40% of the maximum amplitude 41 may be defined as the pseudo systolic blood pressure 46.

Referring back to FIG. 3, the blood pressure calculation unit 511 calculates blood pressure of which an error is to be corrected using a waveform obtained from the filtering unit 3. In an embodiment, the blood pressure of which an error is to be corrected is blood pressure measured at the first site of the first body, and includes at least one of the pseudo diastolic blood pressure 45 and the pseudo systolic blood pressure 46 illustrated in FIG. 4. A method of calculating the pseudo diastolic blood pressure 45 and the pseudo systolic blood pressure 46 is described above in relation to FIG. 4 and thus a detailed description thereof will be omitted.

The error calculation unit 512 corrects a blood pressure value using at least one index obtained from the index determination unit 52 and an error correction equation read from the memory 4.

A method of determining an index in the index determination unit 52 will be described hereinafter in detail.

The index determination unit 52 determines an index which represents a shape of a sphygmogram. The index determination unit 52 determines at least one of a diastolic blood pressure index and a systolic blood pressure index which are values which represent the shape of the sphygmogram. In an embodiment, the index determination unit 52 determines the index using mean arterial pressure obtained from the blood pressure calculation unit 511, and blood pressure of which an error is to be corrected. In an embodiment, when the blood pressure of which an error is to be corrected includes pseudo diastolic blood pressure and pseudo systolic blood pressure, the index determination unit 52 calculates a difference between the mean arterial pressure and the pseudo systolic blood pressure and determines a calculated value of the difference as the systolic blood pressure index. Also, the index determination unit 52 calculates a difference between the mean arterial pressure and the pseudo diastolic blood pressure and determines a calculated value of the difference as the diastolic blood pressure index.

The index determination unit 52 may determine a difference between a blood pressure value where the sphygmogram has maximum amplitude of the sphygmogram measured at a first site of the first body and a blood pressure value of which an error is to be corrected as the index. The blood pressure of which an error is to be corrected generally includes at least one of diastolic blood pressure and systolic blood pressure. However, the blood pressure of which an error is to be corrected is not limited thereto and may include all pressure values sensed by the sensing unit 2. Hereinafter, the blood pressure of which an error is to be corrected is referred to as the diastolic blood pressure and the systolic blood pressure.

In an embodiment, an index is defined as a difference between mean arterial pressure and the blood pressure of which an error is to be corrected. In an embodiment, when the blood pressure of which an error is to be corrected includes the diastolic blood pressure and the systolic blood pressure, the index includes the diastolic blood pressure index and the systolic blood pressure index.

Referring to FIG. 4, the diastolic blood pressure index ("$I_{DBP}$") 47 and the systolic blood pressure index ("$I_{SBP}$") 48 may be respectively defined as Equations 1 and 2.

$$I_{DBP} = MAP - DBP_{pseudo} \quad (1)$$

$$I_{SBP} = SBP_{pseudo} - MAP \quad (2)$$

In Equation 1, $I_{ABP}$ denotes the diastolic blood pressure index 47, MAP denotes the mean arterial pressure 44, and $DBP_{pseudo}$ denotes the pseudo diastolic blood pressure 45. In Equation 2, $I_{SBP}$ denotes the systolic blood pressure index 48, MAP denotes the mean arterial pressure 44, and $SBP_{pseudo}$ denotes the pseudo systolic blood pressure 46.

Referring back to FIG. 3, the error calculation unit 512 corrects the blood pressure measured at the first site of the first body using at least one index obtained from the index determination unit 52 and an error correction equation obtained from the memory 4. The error correction equation represents a correlation between a shape of the sphygmogram measured at one site of the body and a difference between reference blood pressure and blood pressure measured at the one site of a body. In an embodiment, as described above in relation to FIG. 1, the reference blood pressure is blood pressure measured at a second body part, for example, an upper arm having the brachial artery using a noninvasive method, or a wrist having the radial artery using an invasive method. Also, the blood pressure measured at the one site of the body is blood pressure measured at the first body part, for example, a wrist having the radial artery or a finger having the brachial artery. However, the first body part may be determined based on a method of measuring blood pressure to be corrected. In an embodiment, when blood pressure is measured at a finger of the person and the measured blood pressure is to be corrected, the blood pressure measuring apparatus may calculate the error correction equation using the blood pressure measured at the finger as the blood pressure measured at the first site. The shape of the sphygmogram represents a degree of amplitude reduction with reference to a pressure value where the sphygmogram has maximum amplitude, which is the mean arterial pressure, as the pressure value increases and decreases. The error correction equation may be stored in the memory 4 when the blood pressure measuring apparatus is manufactured, and the error correction equation may be changed by, for example, upgrading software, after the blood pressure measuring apparatus is manufactured.

In the error correction equation, an error represents a difference between the blood pressure measured at the first body part and the reference blood pressure, e.g., the blood pressure measured at the second body part. Hereinafter, for convenience of explanation, the first body part is set as a radial artery in a wrist and the second body part is set as a brachial artery in an upper arm. The reference blood pressure may be measured using all of the blood pressure measuring methods described above in relation to FIG. 1. In an embodiment, the reference blood pressure may be measured at the upper arm having the brachial artery using at least one of an auscultatory method, an oscillometric method and a tonometric method. As described above in relation to FIG. 1, a wrist-type or finger-type blood pressure measuring apparatus uses a digital automatic hemadynamometer to measure blood pressure using a noninvasive method. In an embodiment, blood pressure is measured based on a waveform sensed by pressing the first site of the body, e.g., a wrist or a finger. The blood pressure measured at the wrist or the finger may be less accurate than the blood pressure measured at the upper arm having the brachial artery. Thus, an error may be corrected using a difference with the reference blood pressure.

An embodiment of the blood pressure measuring apparatus using a wrist-type digital partial pressing blood pressure measuring method will be described hereinafter.

Figure 5:
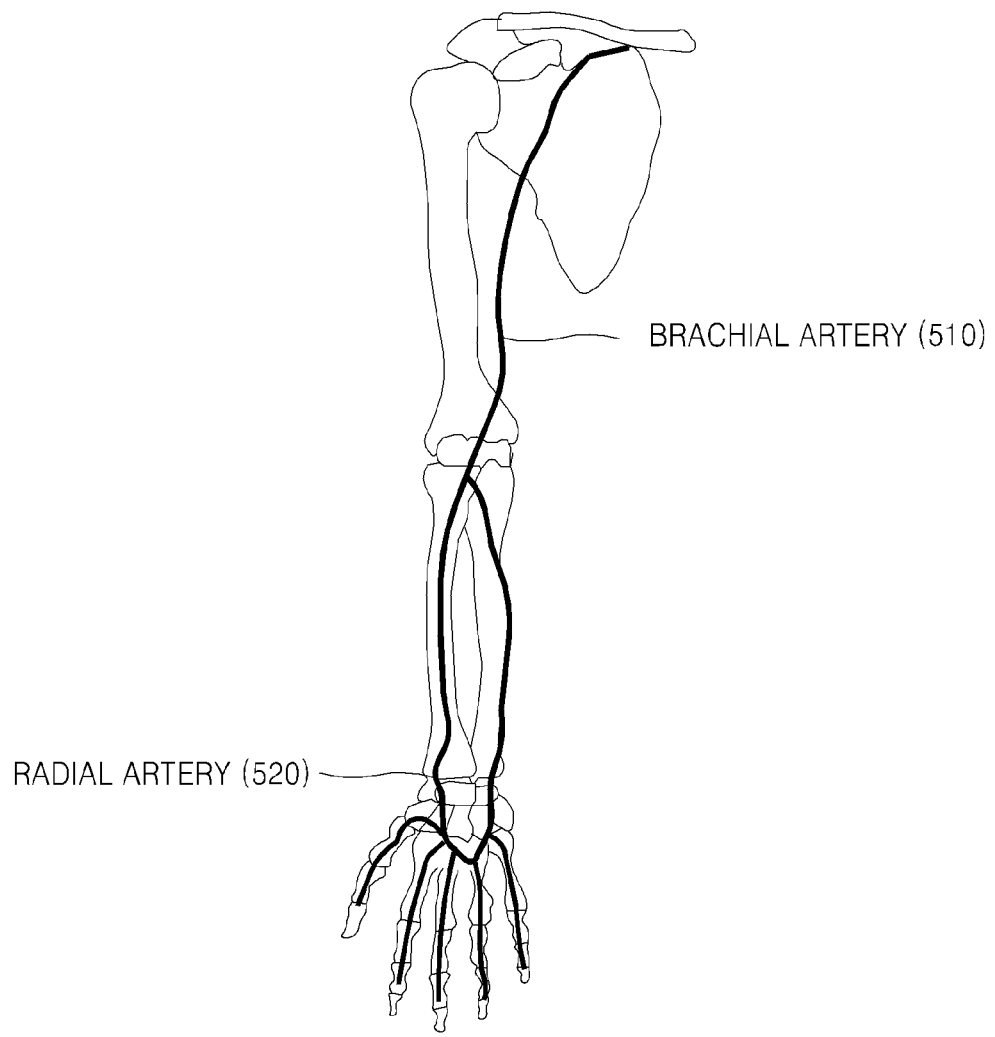
FIG. 5 is a perspective view showing a brachial artery in an upper arm and a radial artery in a wrist.

FIG. 5 is a schematic image showing the brachial artery 510 in an upper arm and the radial artery 520 in a wrist.

As shown in FIG. 5, a waveform sensed by pressing the brachial artery 510 may be set as a waveform of a reference blood pressure. In the wrist-type digital partial pressing blood pressure measuring method, blood pressure is measured at the wrist having the radial artery 520. When the wrist is partially pressed, an appropriate point of the radial artery 520 for measuring the blood pressure may not be properly selected, each person has unique wrist characteristics (for example, the diameter of a bone, the thickness of skin, the content of fat, etc.), and thus blood pressure may not be calculated accurately.

Figure 6:
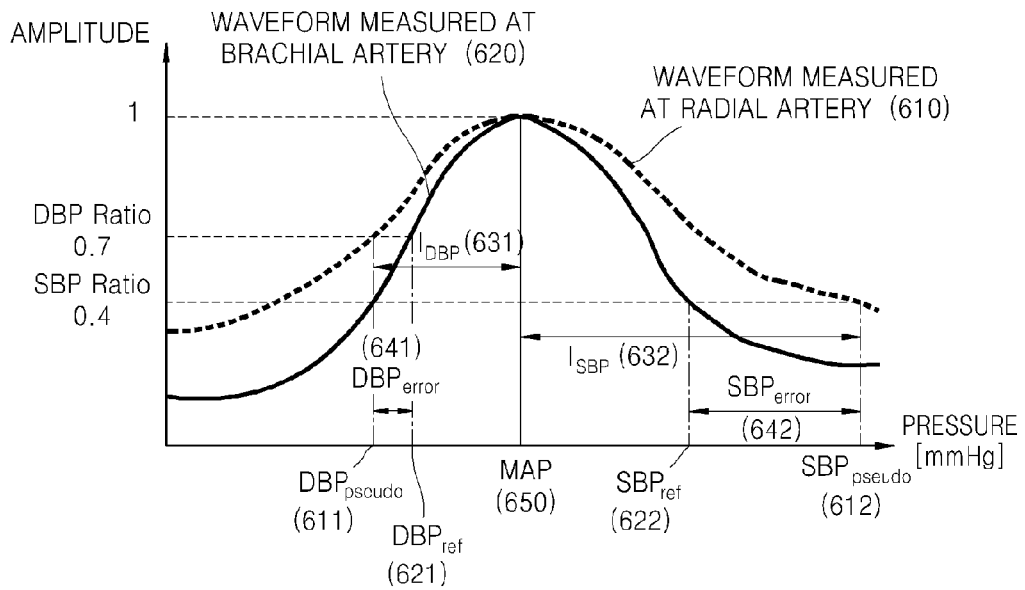
FIG. 6 is a graph of waveforms measured at the brachial artery and the radial artery in FIG. 5.

FIG. 6 is a graph of amplitude in ratio versus pressure of an envelope of a waveform 610 measured at the radial artery and an envelope of a waveform 620 measured at the brachial artery.

The graph of FIG. 6 includes the envelope of the waveform 610 measured at the radial artery, the envelope of the waveform 620 measured at the brachial artery, pseudo diastolic blood pressure 611, pseudo systolic blood pressure 612, reference diastolic blood pressure ("$DBP_{ref}$") 621, reference systolic blood pressure ("$SBP_{ref}$") 622, a diastolic blood pressure index 631, a systolic blood pressure index 632, a diastolic blood pressure error ("$DBP_{err}$") 641, a systolic blood pressure error ("$SBP_{err}$") 642, and mean arterial pressure 650.

The waveform measured at the radial artery and the waveform measured at the brachial artery correspond to pressures on the walls of blood vessels of a person, which are measured at the brachial artery 510 and the radial artery 520 of FIG. 5, respectively. In an embodiment of the blood pressure measuring apparatus of FIG. 1, the waveform measured at the radial artery and the waveform measured at the brachial artery are obtained when the pressing unit 1 presses body sites having the radial artery and the brachial artery, the sensing unit 2 senses pressures on the walls of the radial artery and the brachial artery, the filtering unit 3 filters the sensed pressures, and the envelope of the waveform 610 measured at the radial artery and the envelope of the waveform 620 measured at the brachial artery are calculated y using the filtered pressures and normalized with respect to a value 1.

An envelope is calculated using a signal obtained from the filtering unit 3 and is a curve obtained by dividing the signal into points and connecting maximum values of the points. The maximum values of the points may be calculated using a Hilbert transformation method. In an embodiment, the calculated envelope may be re-calculated using a moving average calculation method and the error correction equation is thereby substantially accurately calculated. A moving average is an average of values calculated at different points to identify a change in trend. The moving average calculation method is a statistical calculation method in which irregular values of sensed pressure are removed to find a long-term trend. When the moving average is calculated, an average of values calculated at N points is referred to as an N point moving average, where N is a natural number. For example, an average of values calculated at three points may be referred to as a three point moving average. After calculating the envelope and the moving average, for convenience of analysis, each waveform may be normalized with respect to a value 1.

As illustrated in FIG. 6, the envelope of the waveform 610 measured at the radial artery and the envelope of the waveform 620 measured at the brachial artery have different shapes, and thus an error occurs in the measurement of diastolic blood pressure and systolic blood pressure. In FIG. 6, a shape of the envelope of the waveform 610 measured at the radial artery is wider than a shape of the envelope of the waveform 620 measured at the brachial artery because a sensor does not accurately sense pressures on the walls of blood vessels due to, for example, the resistance of other parts, the difficulty of finding the location of the radial artery and the inaccuracy of a partial pressing method. Thus, an error in the waveform measured at the radial artery may be calculated with reference to the waveform measured at the brachial artery. In an embodiment, when the blood pressure measuring apparatus uses a wrist-type blood pressure measuring method, an error correction equation is calculated by comparing the waveform measured at the brachial artery to the waveform measured at the radial artery as described above in relation to FIG. 1. However, a method of calculating an error correction equation is not limited thereto. In an embodiment, when the blood pressure measuring apparatus uses a finger-type blood pressure measuring method, the error correction equation is calculated by comparing the waveform measured at the brachial artery to a waveform measured at a finger.

As described above in relation to FIG. 4, points having pre-set ratios with respect to the amplitude of the mean arterial pressure 650 of the waveform measured at the radial artery may be defined as the pseudo diastolic blood pressure 611 and the pseudo systolic blood pressure 612. In an embodiment, when the characteristic ratios are defined as 70% for the diastolic blood pressure and 40% for the systolic blood pressure, the pseudo diastolic blood pressure 611 and the pseudo systolic blood pressure 612 are determined accordingly. When blood pressure calculated using the waveform measured at the brachial artery is a reference blood pressure, the reference diastolic blood pressure 621 and the reference systolic blood pressure 622 may be determined using the same characteristic ratio. Thus, the diastolic blood pressure error 641 and the systolic blood pressure error 642 may be respectively defined as Equations 3 and 4.

$$DBP_{error} = DBP_{pseudo} - DBP_{ref} \qquad (3)$$

$$SBP_{error} = SBP_{pseudo} - SBP_{ref} \qquad (4)$$

In Equation 3, $DBP_{error}$ denotes the diastolic blood pressure error 641, $DBP_{ref}$ denotes the reference diastolic blood pressure 621, and $DBP_{pseudo}$ denotes the pseudo diastolic blood pressure 611. In Equation 4, $SBP_{error}$ denotes the systolic blood pressure error 642, $SBP_{ref}$ denotes the reference systolic blood pressure 622, and $SBP_{pseudo}$ denotes the pseudo systolic blood pressure 612. In an embodiment, the diastolic blood pressure index 631 and the systolic blood pressure index 632 may be respectively defined as Equations 1 and 2. When indices include the diastolic blood pressure index 631 and the systolic blood pressure index 632, and errors include the diastolic blood pressure error 641 and the systolic blood pressure error 642, a graph showing correlations between the indices and the errors may be obtained as illustrated in FIG. 7.

Figure 7:
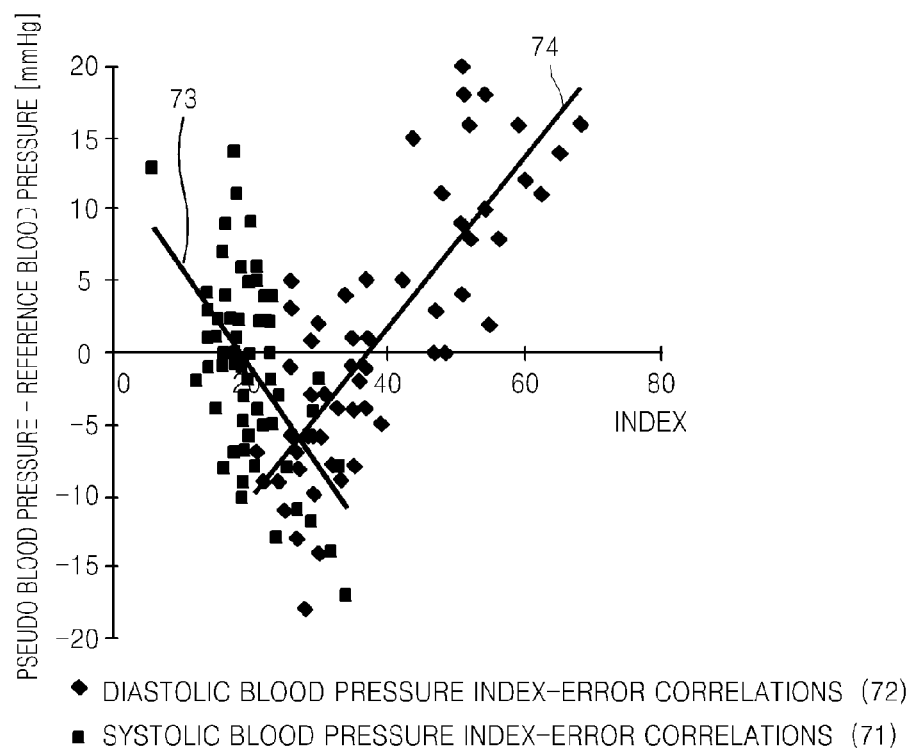
FIG. 7 is a graph showing correlations between indices and errors, according to one or more embodiments.

FIG. 7 is a graph of blood pressure versus index showing correlations between indices and errors, according to an embodiment of the present invention. FIG. 7 will be described in conjunction with FIG. 6.

As shown in FIG. 7, the graph includes diastolic blood pressure index-error correlations 71, systolic blood pressure index-error correlations 72, a diastolic blood pressure index-error correlation trend line 73 and a systolic blood pressure index-error correlation trend line 74.

The indices and errors are calculated using Equations 1 through 4 as described above in relation to FIG. 6 and the calculated results are marked on the graph of FIG. 7 as the diastolic blood pressure index-error correlations 71 and the systolic blood pressure index-error correlations 72. In FIG. 7, each dot is a result of a one-time calculation.

With respect to the diastolic blood pressure index-error correlations 71 and the systolic blood pressure index-error correlations 72, the diastolic blood pressure index-error correlation trend line 73 and the systolic blood pressure index-error correlation trend line 74 may be calculated using various algorithms according to statistical methods. Trend line calculation is performed to analyze a trend in variations and may be performed using, for example, a least mean square ("LMS") algorithm. The LMS algorithm will now be exemplarily described. The diastolic blood pressure index-error correlation trend line 73 is defined so that each of the diastolic blood pressure index-error correlations 71 has a minimum difference from the diastolic blood pressure index-error correlation trend line 73. The diastolic blood pressure index-error correlation trend line 73 and the systolic blood pressure index-error correlation trend line 74 may be defined as Equations 5 and 6.

$$\text{ExpDBP}_{error} = \alpha(I_{DBP}) + \beta \quad (5)$$

$$\text{ExpDBP}_{error} = \gamma(I_{DBP}) + \delta \quad (6)$$

In Equation 5, $\text{ExpDBP}_{error}$ denotes an expected diastolic blood pressure error and $I_{ABP}$ denotes the diastolic blood pressure index 631. In Equation 6, $\text{ExpSBP}_{error}$ denotes an expected systolic blood pressure error and $I_{SBP}$ denotes the systolic blood pressure index 632. Also, $\alpha$, $\beta$, $\gamma$ and $\delta$ are values calculated by using a trend line calculation method according to an embodiment of the present invention. In an embodiment, $\alpha$, $\beta$, $\gamma$, and $\delta$ may be set as $\alpha = -0.5$, $\beta = 10$, $\gamma = 0.5$, and $\delta = -20$, for example. Thus, the expected diastolic blood pressure error and the expected systolic blood pressure error may be calculated using the diastolic blood pressure index 631 and the systolic blood pressure index 632, and the diastolic blood pressure index-error correlation trend line 73 and the systolic blood pressure index-error correlation trend line 74 which are defined by Equations 5 and 6.

Equations 5 and 6 are referred to as error correction equations and the error correction equations may be previously stored in the memory 4. However, Equations 5 and 6 are examples of error correction equations and other error correction equations may be calculated using a trend line calculation method according to the above-described statistical methods.

Referring back to FIG. 3, the blood pressure correction unit 53 calculates an expected blood pressure error using an error correction equation, subtracts the expected blood pressure error from blood pressure of which an error is to be corrected, and thus corrects an error in measured blood pressure. When the blood pressure of which an error is to be corrected includes the diastolic blood pressure and the systolic blood pressure, an expected diastolic blood pressure error and an expected systolic blood pressure error may be calculated using Equations 5 and 6. Pseudo diastolic blood pressure and pseudo systolic blood pressure may be corrected using the expected diastolic blood pressure error and the expected systolic blood pressure error, respectively, as shown in Equations 7 and 8.

$$\text{DBP} = \text{DBP}_{pseudo} - \text{ExpDBP}_{error} \quad (7)$$

$$\text{SBP} = \text{SBP}_{pseudo} - \text{ExpSBP}_{error} \quad (8)$$

In Equation 7, DBP denotes the diastolic blood pressure after correction, $\text{DBP}_{pseudo}$ denotes the pseudo diastolic blood pressure, and $\text{ExpDBP}_{error}$ denotes the expected diastolic blood pressure error. In Equation 8, SBP denotes the systolic blood pressure after correction, $\text{SBP}_{pseudo}$ denotes the pseudo systolic blood pressure and $\text{ExpSBP}_{error}$ denotes the expected systolic blood pressure error. Thus, the blood pressure correction unit 53 corrects the error in the measured blood pressure using Equations 7 and 8 and the output unit 6 receives a corrected blood pressure.

The output unit 6 displays the corrected blood pressure output from the correction unit 5 to a user. The output unit 6 includes a device which displays visual information, such as a display device, a liquid crystal display ("LCD") screen, a light-emitting diode ("LED"), and a division display device, for example, and a device which provides auditory information, such as a speaker, for example.

The control unit 7 controls the pressing unit 1 and the sensing unit 2. In an embodiment, when a user operates the blood pressure measuring apparatus, the control unit 7 obtains a signal input by the user, generates a control signal, and thereby operates the pressing unit 1 and the sensing unit 2. Along with the pressing unit 1 and the sensing unit 2, the control unit 7 may control the other components of the blood pressure measuring apparatus.

Figure 8:
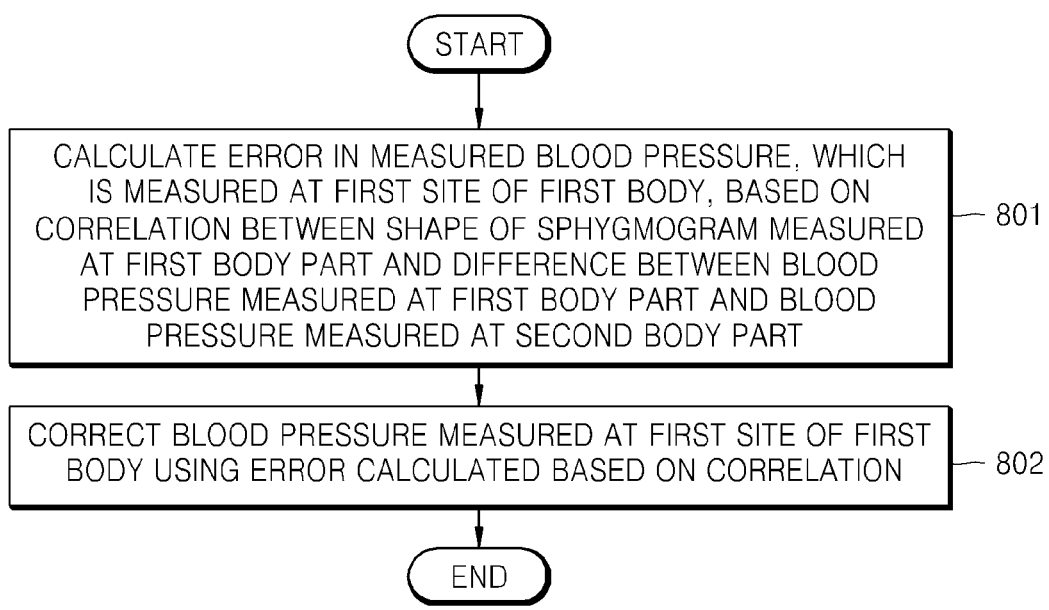
FIG. 8 is a flowchart of a method of correcting an error in blood pressure measurement, according to one or more embodiments.

FIG. 8 is a flowchart of an embodiment of a method of correcting an error in blood pressure measurement according to the present invention.

As shown in FIG. 8, an embodiment of the method includes time-serial operations performed by the blood pressure measuring apparatus in FIG. 1. Thus, FIG. 8 will be described in conjunction with FIG. 1 and any repeated detailed descriptions thereof will hereinafter be omitted. In FIG. 8, for convenience of explanation, it is assumed that a first body part is a site of a human body, a second body part is a second site of a human body and the first body is a body of a person. However, it will be understood that the method according to the current embodiment is not limited thereto.

In operation 801, based on a correlation between a shape of the sphygmogram measured at a first site of a human body and a difference between blood pressure measured at the first site of the human and blood pressure measured at a second site of the human body, the calculation unit 51 calculates an error in blood pressure measured at the first site of a body of a person.

In operation 802, the blood pressure correction unit 53 corrects the blood pressure measured at the first site of the body of the person using the calculated error. The corrected blood pressure may be displayed to a user by the output unit 6.

Figure 9:
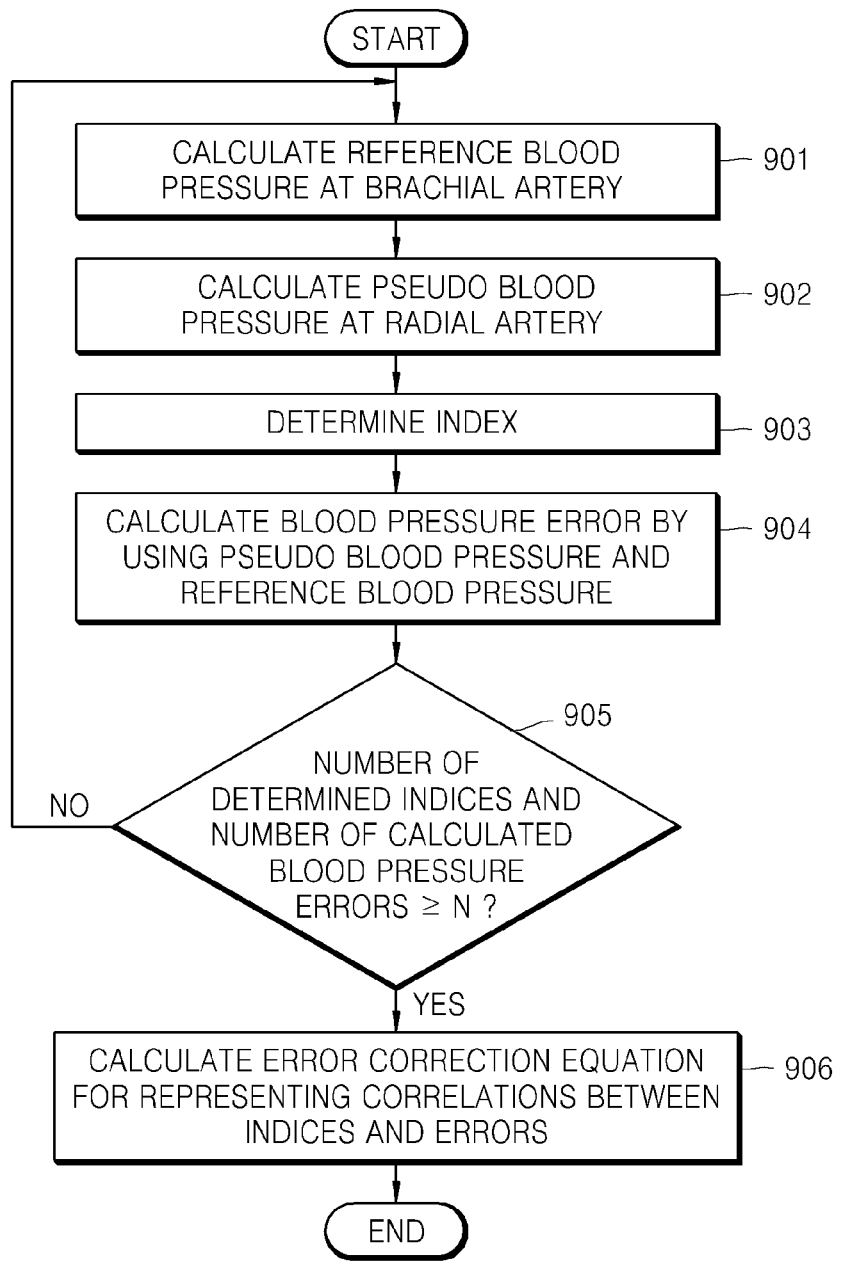
FIG. 9 is a flowchart of a method of calculating an error correction equation in blood pressure measurement, according to one or more embodiments.

FIG. 9 is a flowchart of an embodiment of a method of calculating an error correction equation in blood pressure measurement according to the present invention. In FIG. 9, for convenience of explanation, it is assumed that a first body part is the brachial artery in an upper arm, a second body part is the radial artery in a wrist and blood pressure is measured at the first and second body part using an oscillometric method. However, it will be understood that the method according to the current embodiment is not limited thereto. It will be understood that the blood pressure may be measured at the second body part using an invasive method and may be used as reference blood pressure.

In operation 901, the reference blood pressure is calculated using a waveform measured at the brachial artery in the upper arm. The reference blood pressure may include at least one of reference diastolic blood pressure and reference systolic blood pressure.

In operation 902, pseudo blood pressure is calculated using a waveform measured at the radial artery of the wrist. The pseudo blood pressure includes at least one of pseudo diastolic blood pressure and pseudo systolic blood pressure.

In operation 903, an index is determined as a difference between a blood pressure value where the sphygmogram has a maximum amplitude of a waveform measured at a site of the body and a blood pressure value of which an error is to be corrected. The index includes at least one of a diastolic blood pressure index and a systolic blood pressure index. In an embodiment, the index may be determined using a difference between a blood pressure value where the sphygmogram has the maximum amplitude of the waveform measured at the radial artery of the wrist and the pseudo blood pressure previously calculated.

In operation 904, blood pressure error is calculated using the reference blood pressure calculated and the pseudo blood pressure calculated. In an embodiment, a diastolic blood pressure error is calculated by subtracting the reference diastolic blood pressure from the pseudo diastolic blood pressure and a systolic blood pressure error is calculated by subtracting the reference systolic blood pressure from the pseudo systolic blood pressure.

In operation 905, if the number of indices determined and the number of blood pressure errors calculated are equal to or greater than n (n is a natural number), a trend line which represents correlations between the indices and the blood pressure error is calculated. Otherwise, the reference pressure is re-calculated. N may be an arbitrary number set by a user according to an operation environment. As n increases, the accuracy of a calculated error correction equation may be increased. In an embodiment, n may be, for example, 60.

In operation 906, the trend line which represents correlations between the indices and the blood pressure errors is calculated using the indices determined and the blood pressure errors calculated. The trend line is calculated using an algorithm so that each blood pressure error regarding an index has a minimum difference from the calculated trend line. The trend line calculated using the algorithm corresponds to an error correction equation and may be stored in the memory 4 of the blood pressure measuring apparatus.

Figure 10:
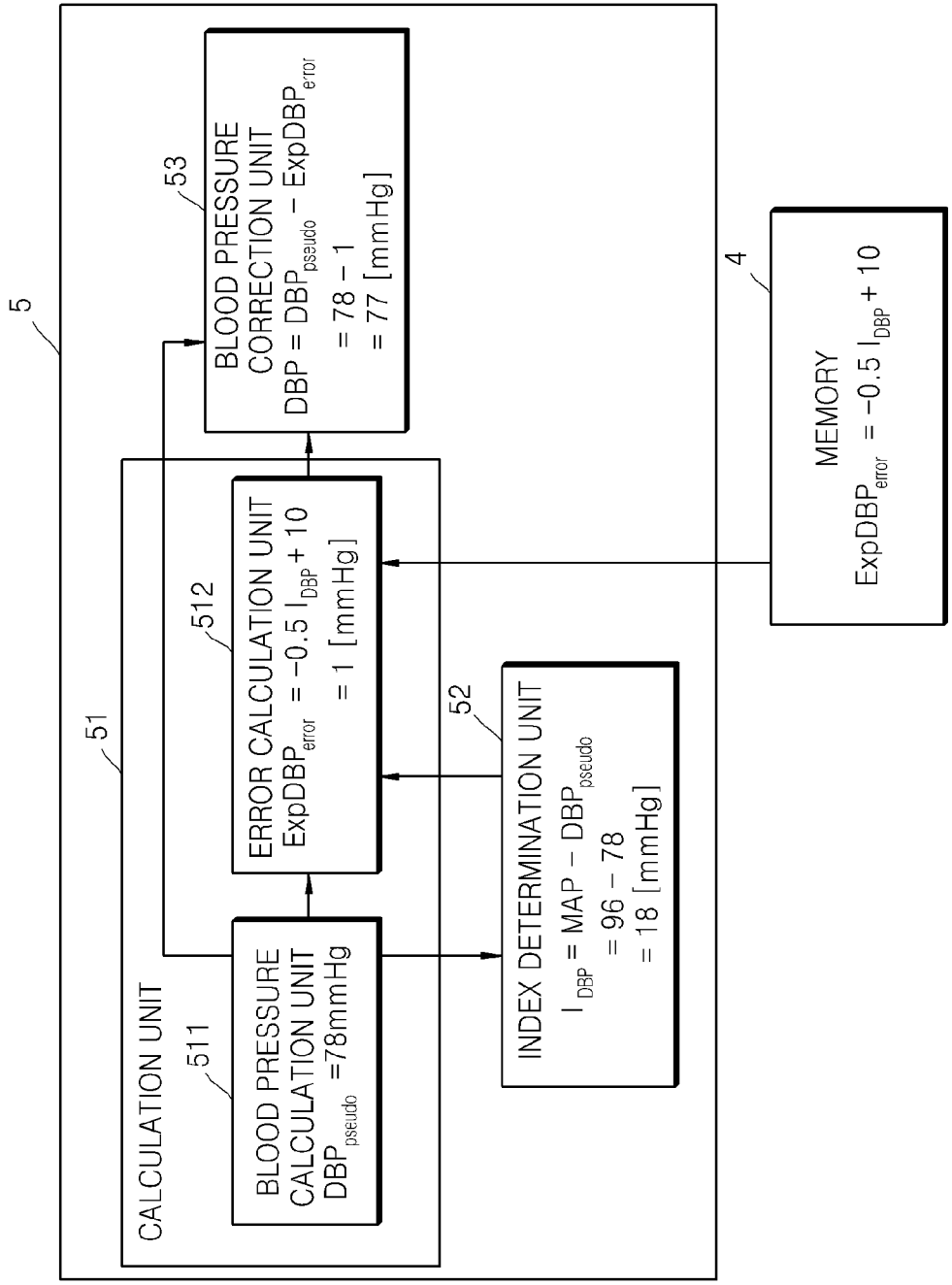
FIG. 10 is a diagram for describing an exemplary case for correcting an error in diastolic blood pressure measurement, according to one or more embodiments.

FIG. 10 is a diagram for describing an exemplary case for correcting an error in diastolic blood pressure measurement, according to an embodiment of the present invention. FIG. 10 will be described in conjunction with FIGS. 1 and 3.

Referring to FIG. 10, for convenience of explanation, only diastolic blood pressure will be described. However, it will be understood that blood pressure of which an error is to be corrected is not limited to the diastolic blood pressure, and may include another type of blood pressure, for example, systolic blood pressure. The memory 4 previously stores an error correction equation for the diastolic blood pressure. The error correction equation for the diastolic blood pressure may be calculated according the method illustrated in FIG. 9 and may be defined by Equation 5. Hereinafter, for convenience of explanation, the error correction equation for the diastolic blood pressure may be defined as Equation 9.

$$\text{ExpDBP}_{error} = -0.5(I_{DBP}) + 10 \tag{9}$$

In Equation 9, $\text{ExpDBP}_{error}$ denotes an expected diastolic blood pressure error and $I_{ABP}$ denotes a diastolic blood pressure index.

The correction unit 5 corrects an error in blood pressure measurement using a waveform of blood pressure measured at a site of a body of a person. The blood pressure calculation unit 511 calculates pseudo diastolic blood pressure using a waveform of blood pressure measured at the site of the first body. In an embodiment, the pseudo diastolic blood pressure is about 78 mmHg.

The index determination unit 52 determines a difference between the pseudo diastolic blood pressure and blood pressure having a maximum amplitude of the waveform of the blood pressure measured at the site of the first body, e.g., mean arterial pressure, as a diastolic blood pressure index. In the current embodiment, if the mean arterial pressure is about 96 mmHg and the pseudo diastolic blood pressure is about 78 mmHg, the diastolic blood pressure index is about 18 mmHg.

The error calculation unit 512 calculates an expected diastolic blood pressure error using the diastolic blood pressure index and the error correction equation, e.g., Equation 9, read from the memory 4. According to Equation 9, the expected diastolic blood pressure error is about 1 mmHg.

The blood pressure correction unit 53 corrects the pseudo diastolic blood pressure by subtracting the expected diastolic blood pressure error from the pseudo diastolic blood pressure. Thus, the corrected diastolic blood pressure is about 77 mmHg.

In an embodiment, the blood pressure measuring apparatus conveniently measures blood pressure at a wrist or a finger using a noninvasive method and substantially increase the accuracy of blood pressure measurement by correcting an error in the measured blood pressure. Thus, blood pressure is conveniently and substantially accurately measured.

As described above, according to the at least one of the above embodiments of the present invention, in a blood pressure measuring apparatus using a noninvasive blood pressure measuring method which measures blood pressure continuously and conveniently, blood pressure measured at the brachial artery using a noninvasive method or measured using an invasive method may be used as reference blood pressure, an error may be corrected with respect to the reference blood pressure, and the blood pressure is thereby substantially accurately measured. In an embodiment, a blood pressure measuring apparatus including a finger-type or wrist-type partial pressing blood pressure measuring apparatus, for example, measures blood pressure substantially accurately and conveniently.

The embodiments of the present invention can be written as computer programs and can be implemented in specific- or general-use digital computers that execute the programs using a computer readable recording medium. Data used in the above-described embodiments can be recorded on a medium in a variety of ways including recording media, such as magnetic storage media, e.g., read only memory ("ROM"), floppy disks, hard disks, and optical recording media, e.g., compact disk read only memory ("CD-ROM") or digital versatile disc ("DVD").

The present invention should not be construed as being limited to the exemplary embodiments set forth herein. Rather, the embodiments described herein are provided so that this disclosure will be thorough and complete and will fully convey the general inventive concept to those of ordinary skill in the art.

While the present invention has been particularly shown and described with reference to exemplary embodiments thereof, it will be understood by those of ordinary skill in the art that various changes in form and details may be made therein without departing from the spirit or scope of the present invention as defined by the following claims.

What is claimed is:

1. A method of correcting an error in a measured blood pressure, the method comprising:
    measuring a blood pressure at a first site of a first body by at least one sensor;
    calculating, using a processor, the error in the blood pressure, which is transmitted by the at least one sensor, based on a correlation between a shape of a sphygmogram measured at a first body part and a difference between a blood pressure measured at the first body and a blood pressure measured at a second body part;
    correcting, using the processor, the blood pressure which is transmitted by the at least one sensor using the calculated error; and
    outputting data corresponding to the corrected blood pressure to an output unit,
    wherein the first body part is one of the first site of the first body and a first site of a second body, which is a same body part as the first site of the first body, and
    the second part is one of a second site of the first body and a second site of the second body,
    wherein the calculation is performed by combining coefficient values and an index corresponding to the shape of the sphygmogram measured at the first body part,
    wherein the index is calculated based on a difference between a maximum amplitude blood pressure at which the sphygmogram measured at the first site of the first body has a maximum amplitude and the blood pressure which is transmitted by the at least one sensor, and
    the coefficient values are determined by using a method of calculating a trend line which indicates a correlation between the index and the error in the blood pressure which is transmitted by the at least one sensor.

2. The method of claim 1, wherein
    the sphygmogram measured at the first body part is measured by pressing the first body part with a pressure which increases during a first period and decreases during a second period, and
    the shape of the sphygmogram measured at the first body part is used to determine a degree of amplitude reduction with respect to a pressure value of the pressure which corresponds to a maximum amplitude of the sphygmogram measured at the first body part.

3. The method of claim 1, wherein the blood pressure measured at the first site of the first body comprises at least one blood pressure at which the sphygmogram has an amplitude in a pre-set ratio with respect to the maximum amplitude.

4. The method of claim 1, wherein the calculating the error comprises using a correlation between the index and the difference between the blood pressure measured at the first body part and the blood pressure measured at the second body part.

5. The method of claim 4, further comprising reading an error correction equation from a memory, the error correction equation being used to determine the correlation between the index and the difference between the blood pressure measured at the first body part and the blood pressure measured at the second body part, wherein the calculating the error comprises substituting the index into the error correction equation.

6. The method of claim 1, wherein the correcting the blood pressure comprises subtracting the calculated error from the blood pressure measured at the first site of the first body.

7. The method of claim 1, further comprising calculating diastolic blood pressure using the sphygmogram measured at the first site of the first body, wherein the determining the index comprises determining a diastolic blood pressure index by subtracting the diastolic blood pressure from the maximum amplitude blood pressure, the calculating the error comprises calculating a diastolic blood pressure error using the diastolic blood pressure index, and the correcting the blood pressure comprises correcting the diastolic blood pressure by subtracting the diastolic blood pressure error from the diastolic blood pressure.

8. The method of claim 1, further comprising calculating systolic blood pressure using the sphygmogram measured at the first site of the first body, wherein the determining the index comprises determining a systolic blood pressure index by subtracting the maximum amplitude blood pressure from the systolic blood pressure, the calculating the error comprises calculating a systolic blood pressure error using the systolic blood pressure index, and the correcting the blood pressure comprises correcting the systolic blood pressure by subtracting the systolic blood pressure error from the systolic blood pressure.

9. The method of claim 1, wherein the blood pressure measured at the second body part is measured using one of an invasive method and a noninvasive method.

10. The method of claim 1, wherein the blood pressure measured at the second body part is measured at a brachial artery in an upper arm of one of the first body and the second body using a noninvasive method.

11. A non-transitory computer readable medium storing instructions which control at least one processor to perform a method of correcting an error in a blood pressure which is measured at a first site of a first body by at least one sensor, the method comprising:
    calculating the error in the measured blood pressure, which is transmitted by the at least one sensor, based on a correlation between a shape of a sphygmogram measured at a first body part and a difference between blood pressure measured at the first body part and blood pressure measured at a second body part;
    correcting the blood pressure which is transmitted by the at least one sensor using the calculated error; and outputting data corresponding to the corrected blood pressure to an output unit,
    wherein the first body part is one of the first site of the first body and a first site of a second body, which is a same body part as the first site of the first body, and
    the second body part is one of a second site of the first body and a second site of the second body,
    wherein the calculation is performed by combining coefficient values and an index corresponding to the shape of the sphygmogram measured at the first body part,
    wherein the index is calculated based on a difference between a maximum amplitude blood pressure at which the sphygmogram measured at the first site of the first body, and
    the coefficient values are determined by using a method of calculating a trend line which indicates a correlation between the index and the error in the blood pressure measured at the first site of the first body.

* * * * *